(12) United States Patent
Xu et al.

(10) Patent No.: US 11,014,885 B2
(45) Date of Patent: May 25, 2021

(54) METHOD FOR PREPARING DONEPEZIL PAMOATE

(71) Applicants: ZHEJIANG HUAHAI PHARMACEUTICAL CO., LTD., Zhejiang (CN); SHANGHAI AOBO PHARMTECH, INC., LTD., Shanghai (CN)

(72) Inventors: Wei Xu, Shanghai (CN); Xi Chen, Shanghai (CN); Hong Gu, Shanghai (CN)

(73) Assignees: Zhejiang Huahai Pharmaceutical Co., Ltd., Zhejiang (CN); Shanghai Aobo Pharmtech, Inc., Ltd., Shanghai (CN)

( * ) Notice: Subject to any disclaimer, the term of this patent is extended or adjusted under 35 U.S.C. 154(b) by 0 days.

(21) Appl. No.: 16/618,896

(22) PCT Filed: Jun. 5, 2018

(86) PCT No.: PCT/CN2018/089999
§ 371 (c)(1),
(2) Date: Dec. 3, 2019

(87) PCT Pub. No.: WO2018/223971
PCT Pub. Date: Dec. 13, 2018

(65) Prior Publication Data
US 2020/0087256 A1   Mar. 19, 2020

(30) Foreign Application Priority Data
Jun. 5, 2017   (CN) .......................... 201710413010.1

(51) Int. Cl.
*C07D 211/32*   (2006.01)
*C07C 63/46*    (2006.01)

(52) U.S. Cl.
CPC ............ *C07D 211/32* (2013.01); *C07C 63/46* (2013.01)

(58) Field of Classification Search
CPC .................................................... C07D 211/32
USPC .......................................................... 546/206
See application file for complete search history.

(56) References Cited

U.S. PATENT DOCUMENTS 9,353,059 B2 *  5/2016  Gu ........................ C07D 211/32
2008/0076928 A1   3/2008  Tarur et al.

FOREIGN PATENT DOCUMENTS

| CN | 104039765 A | 9/2014 |
| WO | WO 2013/005094 A1 | 1/2013 |
| WO | WO 2013/078608 A1 | 6/2013 |
| WO | 2018153315 * | 8/2018 |

OTHER PUBLICATIONS

Extended European Search Report (EESR) of EP Application No. 18813380.5, dated Mar. 30, 2020 (6 pages).
Nicole Steiger et al., *Recrystallization of Active Pharmaceutical Ingredients*, Crystallization—Science and Technology, Sep. 19, 2012, InTech, XP055410247, ISBN: 978-953-51-0757-6, pp. 183-204, DOI: 10.5772/52725.

* cited by examiner

*Primary Examiner* — Niloofar Rahmani
(74) *Attorney, Agent, or Firm* — Alston & Bird LLP

(57) ABSTRACT

Disclosed is a new method for preparing a donepezil pamoate (1-benzyl-4-[(5,6-dimethoxyindan-2-one)methyl]piperidine pamoate). The donepezil pamoate prepared by using the method has a high purity and a good flowability.

5 Claims, 2 Drawing Sheets

METHOD FOR PREPARING DONEPEZIL PAMOATE

The present application claims the priority of Chinese Patent Application No. 201710413010.1, with the title of "NEW METHOD FOR PREPARING DONEPEZIL PAMOATE", filed before the CNIPA on Jun. 5, 2017, which is herein incorporated by reference in its entirety.

FIELD OF THE INVENTION

The present application relates to a new method for preparing a donepezil pamoate (1-benzyl-4-[(5,6-dimethoxyindan-2-one)methyl]piperidine pamoate), which belongs to the field of chemical medicine.

BACKGROUND OF THE INVENTION

The chemical name of donepezil is 1-benzyl-4-[(5,6-dimethoxyindan-2-one)methyl]piperidine, which is a drug for treatment of Alzheimer's disease with a molecular weight of 379.49 and a melting point of 207° C.

Alzheimer's disease can cause symptoms of dementia in patients, including memory loss, slow thinking, and limited daily activities. Patients with Alzheimer's disease are often non-compliant, and it is difficult to estimate whether the patient has received the exact dose of the drug. Therefore, it is necessary to formulate donepezil into a sustained release preparation by means of salt formation.

Patent CN201280058819 discloses donepezil pamoate crystal form A, B and a preparation method thereof. The solvent used is DMSO and water. The starting materials are donepezil free base or donepezil hydrochloride, and pamoic acid or pamoic acid disodium salt.

Patent WO2013005094 discloses donepezil pamoate crystal form T1, T2, T3 and a preparation method thereof. The solvent used includes methanol, isopropanol, DMF and water. The starting materials are donepezil free base and pamoic acid. The powder properties of the donepezil pamoate prepared by the above method have technical problems such as severe agglomeration and poor fluidity, which makes it difficult for subsequent drug development. Through continuous research, the inventors have discovered a novel method for preparing donepezil pamoate, which overcomes the problems of the prior art.

SUMMARY OF THE INVENTION

The present invention provides a method for preparing donepezil pamoate (compound of formula I).

Furthermore, the present invention provides a method for preparing donepezil pamoate, wherein the method comprises dissolving the compound of formula I in an organic solvent and adding another solvent dropwise to precipitate it. Furthermore, the present invention provides a method for preparing donepezil pamoate, wherein the reaction solvent is one selected from the group consisting of alcohols, ethers, esters, ketones, nitriles, alkanes and water, or a combination thereof.

Furthermore, the present invention provides a method for preparing donepezil pamoate, wherein the reaction solvent is ketones.

Furthermore, the present invention provides a method for preparing donepezil pamoate, wherein the reaction solvent is acetone.

Furthermore, the present invention provides a method for preparing donepezil pamoate, wherein dissolving is carried out at a temperature of from 0 to 50° C. Furthermore, the present invention provides a method for preparing donepezil pamoate, wherein dissolving is carried out at a temperature of from 15 to 30° C. Furthermore, the present invention provides a method for preparing donepezil pamoate, wherein another solvent is one selected from the group consisting of alcohols, ethers, esters, ketones, nitriles, alkanes and water, or a combination thereof.

Furthermore, the present invention provides a method for preparing donepezil pamoate, wherein another solvent is water.

Furthermore, the present invention provides a method for preparing donepezil pamoate, wherein adding another solvent dropwise is carried out at a temperature of 0 to 50° C.

Furthermore, the present invention provides a method for preparing donepezil pamoate, wherein adding another solvent dropwise is carried out at a temperature of 15 to 30° C.

The compound of formula I according to the invention is crystal form A according to the X-ray powder diffraction spectrum (see FIG. 1) using Cu—K alpha radiation and the DSC-TGA pattern.

The compound of formula I according to the invention has an angle of repose of <30° and good fluidity.

DESCRIPTION OF THE DRAWINGS

In order to illustrate the examples of the present invention and the prior art more clearly, following are brief descriptions for the drawings used in the examples and the prior art. It is obvious to those skilled in the art that the drawings in the following description are only some examples of the

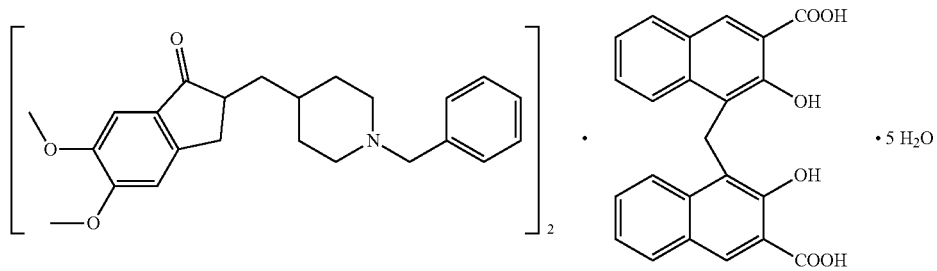

Formula I invention, and other drawings may be obtained from these drawings without any inventive effort.

Figure 1:
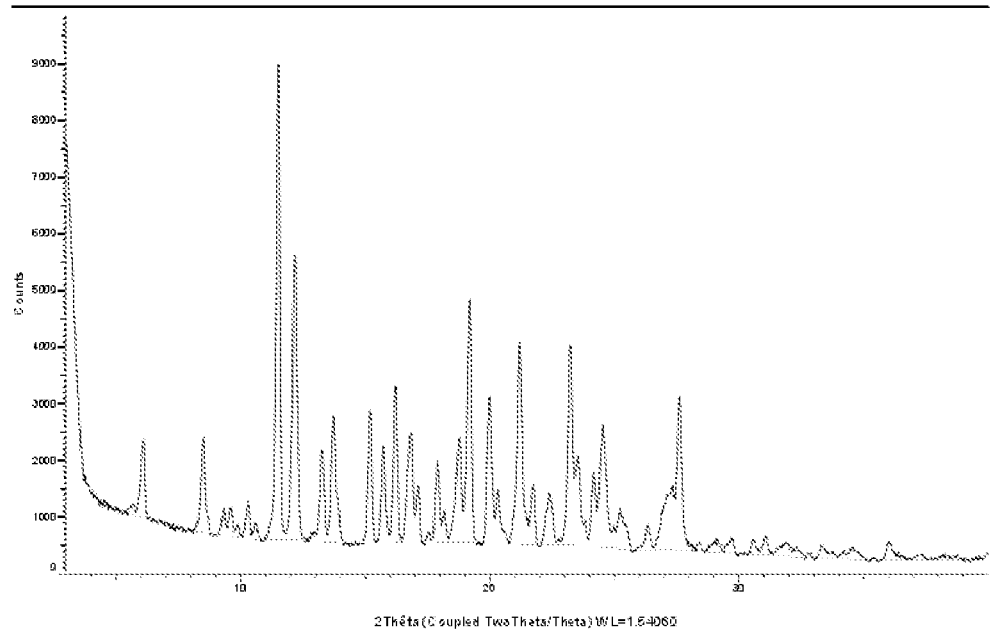

FIG. 1 is an XRPD pattern of donepezil pamoate.

Figure 2:
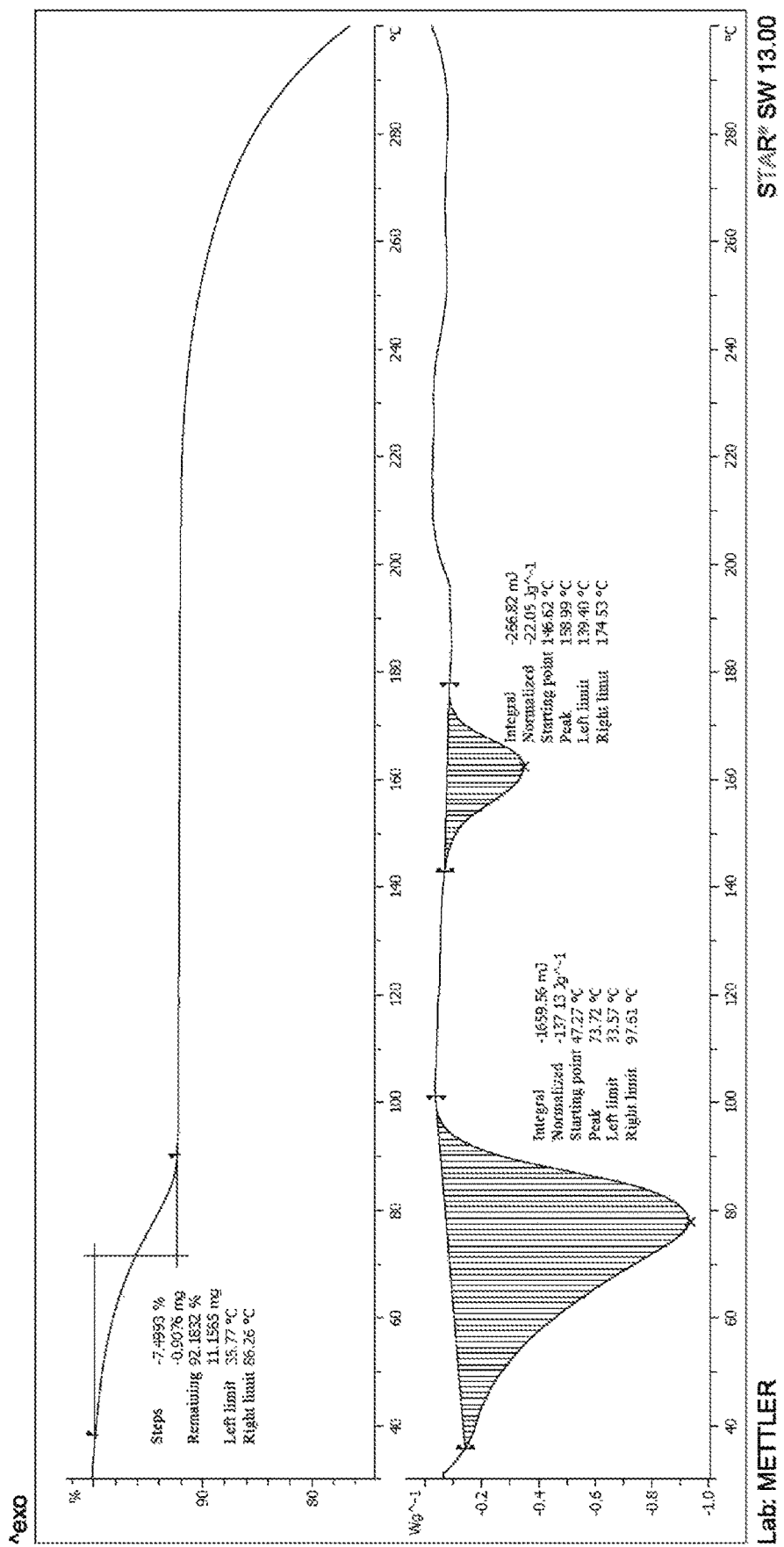

FIG. 2 is a DSC-TGA pattern of donepezil pamoate.

DETAILED DESCRIPTION OF THE INVENTION

The examples of the present invention will be described in detail below with reference to the examples. The examples of the present invention include, but are not limited to, the following examples, which are not intended to limit the scope of the invention.

The X-ray powder diffraction data of the present invention was measured by BRUKER D8 Advance of Bruker Germany Corporation, voltage and current: 40 kV, 40 mA; goniometer: vertical goniometer, radius 280 mm; slit: DS=2°, SS=½°, mask=15 mm, RS=5.0 mm; detector: LYNXEYE detector; scanning mode: continuous scanning; scanning range: 3-40°; counting time per step: 0.2 s; total scanning time: 390 s.

The differential scanning calorimetry pattern of the present invention was measured by TGA/DSC 2 from METTLERSwitzerland Corporation, with a temperature range of 30-300° C. and a temperature increase rate of 10° C./min.

Example 1: Preparation of Donepezil Pamoate 5 ml of acetone was added to 200 mg of donepezil pamoate sample to completely dissolve it at room temperature. 15 ml of water was added dropwise at room temperature. Solids appeared immediately during the addition and dispersed well. After the addition was completed, stirring was continued for 2 hours and then the reaction mixture was filtered. The filter cake was washed with 50 ml of water, filtered under vacuum for 10 min and dried in vacuo to obtain 180 mg of donepezil pamoate sample. The crystal form of the obtained sample was Form A.

Example 2: Preparation of Donepezil Pamoate 50 ml of acetone was added to 2 g of the donepezil pamoate sample to completely dissolve it at room temperature. 150 ml of water was added dropwise at room temperature. Solids appeared immediately during the addition and dispersed well. After the addition was completed, stirring was continued for 2 hours and then the reaction mixture was filtered. The filter cake was washed with 50 ml of water, filtered under vacuum for 10 min and dried in vacuo to obtain 1.8 g of donepezil pamoate sample. The crystal form of the obtained sample was Form A.

Example 3: Preparation of Donepezil Pamoate 500 ml of acetone was added to 20 g of the donepezil pamoate sample to completely dissolve it at room temperature. 1.5 L of water was added dropwise at room temperature. Solids appeared immediately during the addition and dispersed well. After the addition was completed, stirring was continued for 2 hours and then the reaction mixture was filtered. The filter cake was washed with 500 ml of water, filtered under vacuum for 10 min and dried in vacuo to obtain 18 g of donepezil pamoate sample. The crystal form of the obtained sample was Form A.

The above are only preferred examples of the present invention, and are not intended to limit the present invention. Any modifications, equivalents, improvements, etc., which are made within the spirit and principles of the present invention, should be included within the scope of the present invention.

The invention claimed is:

1. A method for preparing a crystal form A of a compound of formula I, comprising dissolving the compound of formula I in a reaction solvent and adding another solvent dropwise for precipitation to give the crystal form A of the compound of formula I, wherein the reaction solvent is acetone, and wherein another solvent is water.

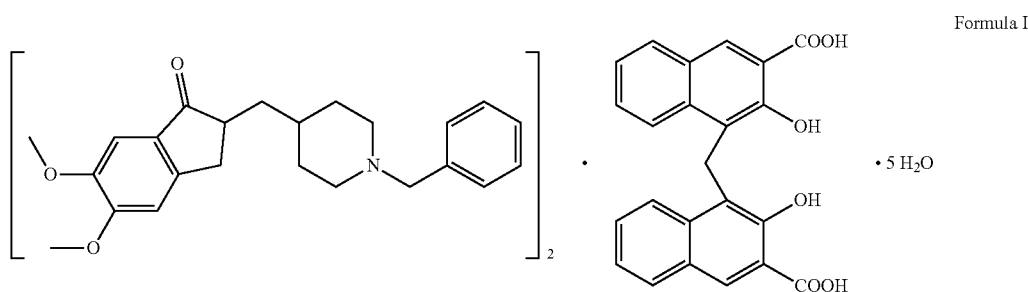

Formula I

2. The method according to claim 1, wherein dissolving is carried out at a temperature of from 0 to 50° C.

3. The method according to claim 1, wherein dissolving is carried out at a temperature of from 15 to 30° C.

4. The method according to claim 1, wherein adding another solvent dropwise is carried out at a temperature of 0 to 50° C.

5. The method according to claim 1, wherein adding another solvent dropwise is carried out at a temperature of 15 to 30° C.

* * * * *